(12) United States Patent
Roy et al.

(10) Patent No.: US 8,852,566 B2
(45) Date of Patent: Oct. 7, 2014

(54) COMPOSITIONS AND METHODS FOR PREFERENTIAL DISTRIBUTION OF ACTIVE AGENTS TO INJURY SITES

(75) Inventors: Josee Roy, Memphis, TN (US); Toya Kimble, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 611 days.

(21) Appl. No.: 12/411,572

(22) Filed: Mar. 26, 2009

(65) Prior Publication Data

US 2010/0247677 A1      Sep. 30, 2010

(51) Int. Cl.

| | |
|---|---|
| A61K 31/765 | (2006.01) |
| A61K 45/06 | (2006.01) |
| A61K 47/10 | (2006.01) |
| A61K 33/06 | (2006.01) |
| A61K 9/00 | (2006.01) |
| A61K 33/14 | (2006.01) |
| C07C 31/20 | (2006.01) |
| C07F 3/02 | (2006.01) |

(52) U.S. Cl.
CPC ............... *A61K 9/0019* (2013.01); *A61K 45/06* (2013.01); *A61K 47/10* (2013.01); *A61K 33/06* (2013.01)
USPC ....... 424/77; 424/78.08; 424/78.37; 424/722; 514/738; 514/789

(58) Field of Classification Search
USPC ........ 424/73.38, 9.1, 78.06, 78.1, 78.37, 131, 424/187, 227, 423, DIG. 13; 514/45, 251, 514/283
See application file for complete search history.

(56) References Cited

U.S. PATENT DOCUMENTS

| | | | |
|---|---|---|---|
| 3,026,248 A | 3/1962 | Noseworthy et al. | |
| 4,020,162 A | 4/1977 | Ghilardi et al. | |
| 4,451,447 A | 5/1984 | Kaplan et al. | |
| 5,605,687 A * | 2/1997 | Lee ............................ | 424/78.06 |
| 6,841,551 B2 * | 1/2005 | Nimmo et al. ............. | 514/230.8 |
| 7,582,680 B1 | 9/2009 | Shi et al. | |

(Continued)

FOREIGN PATENT DOCUMENTS

| | | |
|---|---|---|
| GB | 1250304 A | 10/1971 |
| GB | 1286351 A | 8/1972 |
| WO | WO0128544 A | 4/2001 |
| WO | 2002092107 | 11/2002 |

OTHER PUBLICATIONS

Johnson et al., "Clinical Investigation of Intermediate- and High-Purity Antihaemophilic Factor (Factor VIII) Concentrates," 1971, British Journal of Haematology, vol. 21, Issue 1, pp. 21-41.*

(Continued)

*Primary Examiner* — Jane C Oswecki
(74) *Attorney, Agent, or Firm* — William D. Schmidt; Sorell, Lenna & Schmidt, LLP

(57) ABSTRACT

Compositions are provided for preferential distribution of active agents to injury sites. Such compositions may comprise a ligand with hydrophilic properties and one or more active agents, such as compounds comprising hydrophilic metal ions. Because the delivery ligand and the active agent are specifically selected so the interactions between them are mainly of an ionic nature so that binding of the active agent to the delivery ligand and release of the active agent into the target site are not dependent on enzymatic activity. Methods of using such compositions are also disclosed.

26 Claims, 8 Drawing Sheets

(56) References Cited

U.S. PATENT DOCUMENTS

| | | | |
|---|---|---|---|
| 7,837,987 B2 * | 11/2010 | Shi et al. | 424/78.37 |
| 2003/0118545 A1 | 6/2003 | Shi et al. | |
| 2004/0214790 A1 | 10/2004 | Borgens | |
| 2005/0069520 A1 | 3/2005 | Shi et al. | |
| 2007/0258938 A1 * | 11/2007 | Roy et al. | 424/78.3 |
| 2007/0259044 A1 * | 11/2007 | Roy et al. | 424/486 |

OTHER PUBLICATIONS

Johnson et al., "Clinical Investigation of Intermediate- and High-Purity Antihaemophilic Factor (Factor VIII) Concentrates," 1971, British Journal of Haematology, 21(1): 21-41.*

Webster et al., "Pegylated Proteins", 2007, Drug Metabolism and Disposition, 35(1): 9-16.*

Saver et al., "Prehospital Neuroprotective Therapy for Acute Stroke," 2004, Stroke, 35: 106-108.*

Kaptanoglu et al., "Effect of magnesium sulfate in experimental spinal cord injury: evaluation with ultrastructural findings and early clinical results," 2003, J. Clin. Neuroscience, 10(3): 329-334.*

Borgens et al., "Rapid Recovery from Spinal Cord Injury after Subcutaneously Administered Polyethylene Glycol," 2001, J. Neuroscience Research, 66: 1179-1186.*

Ditor et al., "Effect of Polyethylene Glycol and Magnesium Sulfate Administration on Clinically Relevant Neurological Outcomes after Spinal Cord Injury in the Rat," 2007, J. Neuroscience Research, 85: 1458-1467.*

Webster et al., "Pegylated Proteins", 2007, Drug Metabolism and Disposition, vol. 35, Issue No. 1, pp. 9-16.*

Webster et al., "Pegylated Protein", 2007, Drug Metabolism and Disposition, vol. 35, Issue No. 1, pp. 9-16.*

Pelham et al., "Clinical trial—single- and multiple-dose pharmacokinetics of polyethylene glycol (PEG-3350) in healthy young and elderly subjects," 2008, Alimentary Pharmacology & Therapeutics, 28:256-265.*

Simpson et al., "Intrathecal magnesium sulfate protects the spinal cord from ischemic injury during thoracic aortic cross-clamping,"; Anesthesiology (1994) vol. 81, pp. 1493-1499.

Lang-Lazdunski et al., "Prevention of ischemic spinal cord injury: comparative effects of magnesium sulfate and riluzole,"Journal of Vascular Surgery (Jul. 2000); vol. 32; No. 1; pp. 179-189.

Ancill, R.J., "The blood volume of the normal guinea-pig," J. Physiol. (1956)I32, pp. 469-475.

Kaptanoglu et al., "Effects of magnesium sulphate in experimental spinal cord injury: evaluation with ultrastructural findings and early clinical results," Journal of Clinical Neuroscience (2003); vol. 10, No. 3, pp. 329-334.

Borgens R B and Bohnert D., "Rapid recovery from spinal cord injury after subcutaneously administered polyetheylene glycol," Journal of Neuroscience Research (2001); vol. 66, pp. 1179-1186.

Ditor D S et al., "Effects of polyethylene glycol and magnesium sulfate administration on cinically relevant neurological outcomes after spinal cord injury in the rat," Journal of Neuroscience Research (2007); vol. 85, pp. 1458-1467.

The International Search Report and the Written Opinion of the International Searching Authority in PCT/US2007/067580.

Turner, et al., "Magnesium gluconate offers no more protection than magnesium sulphate following diffuse traumatic brain injury in rats.", Journal of the American College of Nutrition. 23(51 (2004), 541S-544S.

Muir, et al., "Magnesium for acute stroke (Intravenous Magnesium Efficacy in Stroke trial): randomised controlled trial.", The Lancet, 363(9407). (Feb. 7, 2004). 439-45.

Saver, et al., "Prehospital Neuroprotective Therapy for Acute Stroke: Results of the Field Administration of Stroke Therapy-Magnesium (FAST-MAG) Pilot Trial.", Stroke, 35(5). (2004). 106-108.

Bittner, et al., "Reconnection of severed nerve axons with polyethylene glvcol.". Brain Research, 367(1-2), (1986), 351-355.

McIntosh, et al., "Magnesium protects against neurological deficit after brain injury.". Brain Research. 482(2). (1989). 252-260.

Shapiro, et al., "Oscillating field stimulation for complete spinal cord injury in humans: a Phase 1 trial.", J. Neurosurg Spine, 2(1), (Jan. 2005), 3-10.

Resende, et al., Local transcutaneous electrical stimulation (TENS) effects in experimental inflammatory edema and pain, European Journal of Pharmacology 504(1) (2004), 217-222.

Kwon, et al. "Magnesium Chloride in a Polyethylene Glycol Formulation as a Neuroprotective Therapy for Acute Spinal Cord Injury: Preclinical Refinement and Optimization," Journal of Neurotrauma 26, 1379-1393 (Aug. 2009).

Kwon, et al. "A Grading System to Evaluate Objectively the Strength of Pre-Clinical Data of Acute Neuroprotective Therapies for Clinical Translation in Spinal Cord Injury," Journal of Neurotrauma, 28, 1525-1543 (Aug. 2011).

Kwon, et al. "Translational Research in Spinal Cord Injury: A Survey of Opinion from the SCI Community," Journal of Neurotrauma, 27, pp. 21-33 (Jan. 2010).

McKee, et al. "Analysis of the Brain Bioavailability of Peripherally Administered Magnesium Sulfate: A Study in Humans with Acute Brain Injury Undergoing Prolonged Induced Hypermagnesemia," Crit. Care Med., 33(3), 661-666 (Mar. 2005).

Journal of Spinal Cord Medicine, 34(6), 620-621 (2011).

* cited by examiner

CSF level of magnesium following administration of magnesium within formulations containing different concentrations of PEG CSF level of magnesium following administration of a magnesium in PEG solution over various delivery periods PEG systemic exposure and half-life following administration of a
magnesium in PEG solution

|  | Parameters evaluated | 10ml/kg of Magnesium in PEG formulation | | 20ml/kg of Magnesium in PEG formulation | |
| --- | --- | --- | --- | --- | --- |
|  |  | Male | Female | Male | Female |
| Single administration | Cmax (μg/mL) | 7378 | 7444 | 13153 | 10158 |
|  | AUC$_{0-\infty}$ (μg×hr/mL) | 7747 | 6539 | 13737 | 10521 |
|  | T$_{½}$ (hr) | 0.51 | 0.49 | 0.55 | 0.54 |
| Repeated administration | Cmax (μg/mL) | 5489 | 2703 | 10896 | 16683 |
|  | AUC$_{0-\infty}$ (μg×hr/mL) | 5089 | 2955 | 14018 | 14975 |
|  | T$_{½}$ (hr) | 0.69 | 0.62 | 0.52 | 0.54 |

Fig. 8

COMPOSITIONS AND METHODS FOR PREFERENTIAL DISTRIBUTION OF ACTIVE AGENTS TO INJURY SITES

FIELD OF THE INVENTION

This invention relates to methods and compositions for targeted drug delivery.

BACKGROUND OF THE INVENTION

Targeted delivery of therapeutic agents to specific organs is a highly challenging, exponentially developing area of experimental and translational biomedicine. In traditional drug delivery system, after a patient is administered a therapeutic agent, the agent is distributed throughout the patients' body via the systemic blood circulation. Because only a small amount of the therapeutic agent can reach the organ on which it needs to act, a high initial dose of the therapeutic agent needs to be administered to the patient. Administering a high dose of therapeutic agent to a patient is likely to increase the systemic concentration of the therapeutic agent, which may have an adverse effect on the patient's healthy organs. If targeted delivery is successful, it would result in a significant reduction in drug toxicity, reduction of the drug dose, and increased treatment efficacy.

Accordingly, there is a need in the art for compositions and methods that enable targeted delivery of therapeutic agents to specific organs.

SUMMARY OF THE INVENTION

One aspect of the invention provides compositions for preferential distribution of one or more active agents to an injury site. Such compositions may comprise a delivery ligand and at least one active agent, preferably a metal ion, capable of forming ionic bonds with the delivery ligand.

In various embodiments, the composition comprises between about 10 and about 60% weight per volume of the delivery ligand, which may be selected from ligands with hydrophilic properties.

The active agent can comprise a metal ion capable of forming ionic bonds with the delivery ligand through electrostatic attraction to chelation sites, i.e. certain heteroatoms of the delivery ligand, for example, N, O, and S atoms, of the delivery ligand. The type of ionic bond can vary including electron sharing between one or more metal molecule and one or more subunit present on one or more ligand molecules. In some embodiments, the active agent comprises a magnesium ion present in concentration of about 0.1 to about 20% weight per volume.

The concentration of the delivery ligand in the instant compositions depends on the number of chelation sites. Since the delivery ligands are composed of repetitions of one or more sub-units (monomers), the number of chelation sites is proportional to the molecular weight of the ligand, with higher concentrations necessary for lower molecular weight ligands to achieve preferential distribution of the active agent to the injured site. One suitable delivery ligand comprises polyethylene glycol (PEG).

Another aspect provides methods of preferential distribution of one or more active agents to an injury site. The methods comprise identifying a patient having an organ affected by a biological condition known to cause vessels supplying the organ to leak, and administering to the patient a therapeutically effective amount of composition as described above.

Yet another aspect provides methods of treating organs affected by one or more biological conditions known to cause vessels supplying the organ to leak by preferentially distributing one or more active agent(s) known to treat the one or more biological conditions. Such methods comprise identifying a patient having such an organ and administering, preferably parenterally, to the patient a therapeutically effective amount of composition as described above.

The therapeutically effective amount can be calculated based on the weight of the patient. Generally, a patient needs to receive a dose of at least about 0.5 to about 10 ml of composition per kg of patient's weight. In the instant methods, at least one dose can be administered within two half-lives of the delivery ligand. In some embodiments, at least one dose can be administered within one half-life of the delivery ligand.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 8 presents a graph showing PEG systemic exposure and half-life following administration of a magnesium in PEG formulation.

Figure 1:
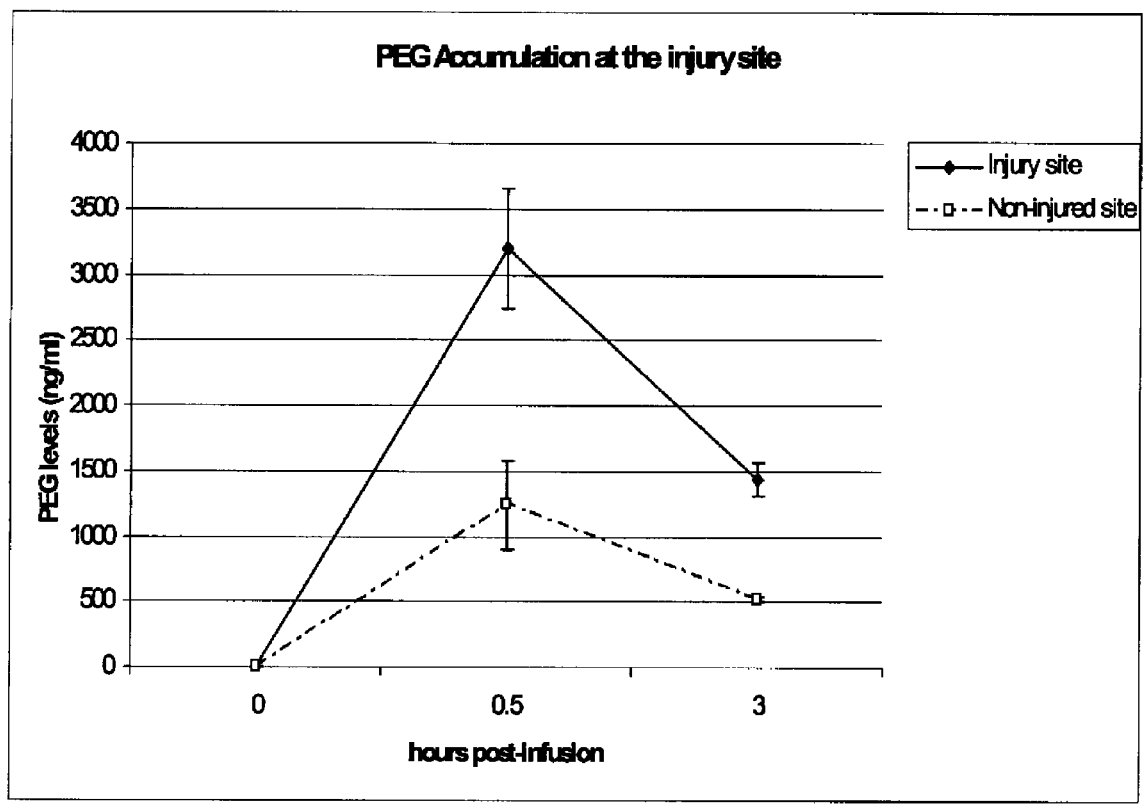
FIG. 1 presents a graph comparing preferential distribution of PEG in the injured site of the central nervous system tissue relative to a non-injured site following parenteral administration of a magnesium in PEG formulation initiated a few hours after injury.
Figure 2:
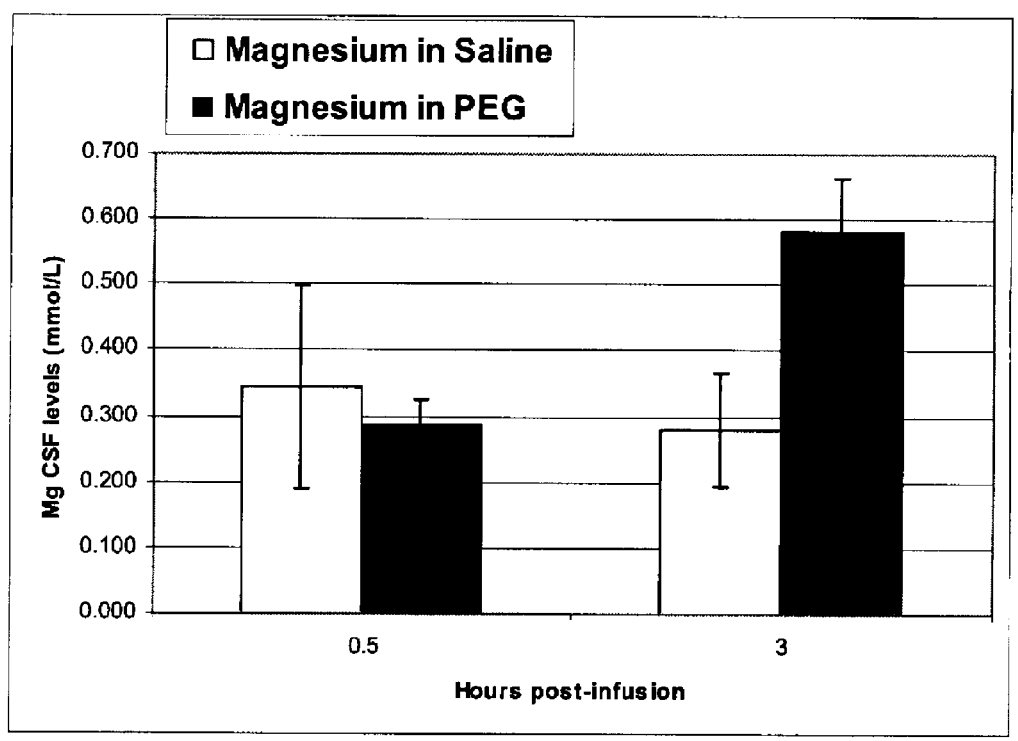
FIG. 2 presents a graph showing preferential distribution of magnesium into the cerebrospinal fluid (CSF) following parenteral administration of magnesium in a PEG formulation relative to a magnesium in saline formulation initiated a few hours after injury.
Figure 3:
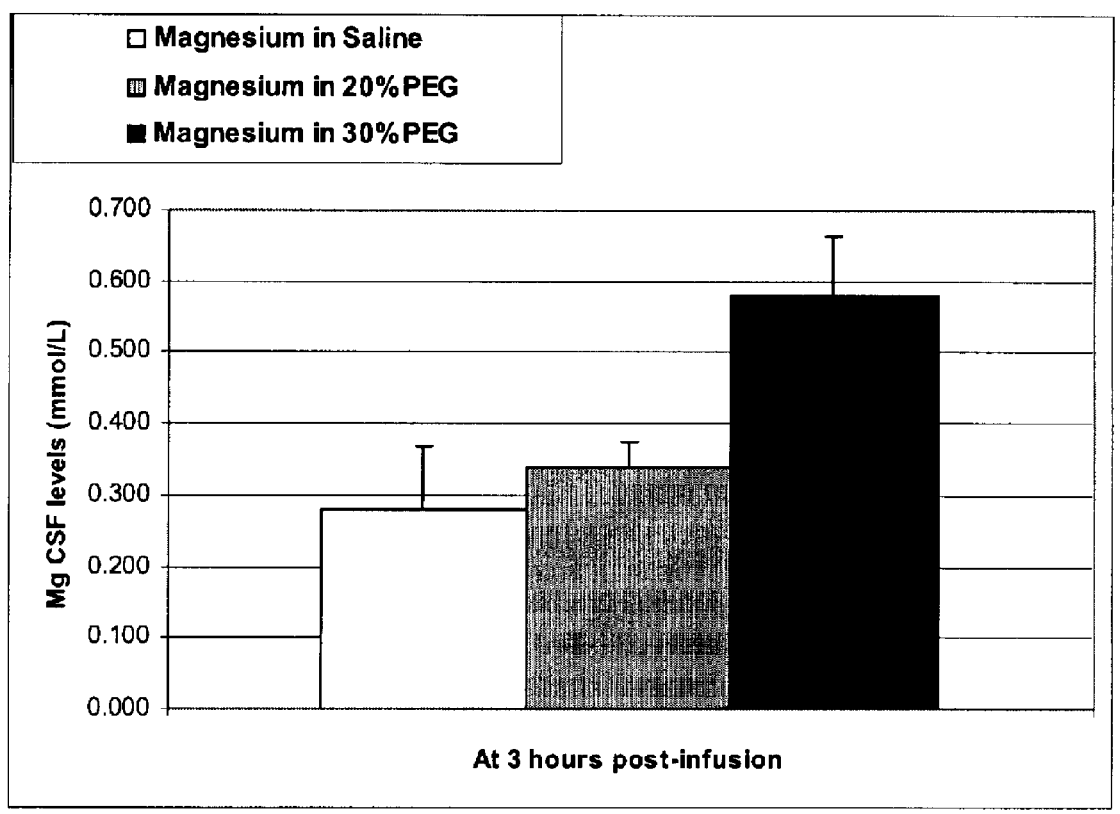
FIG. 3 presents a graph comparing CSF level of magnesium following parenteral administration of magnesium in formulations containing various concentrations of PEG.
Figure 4:
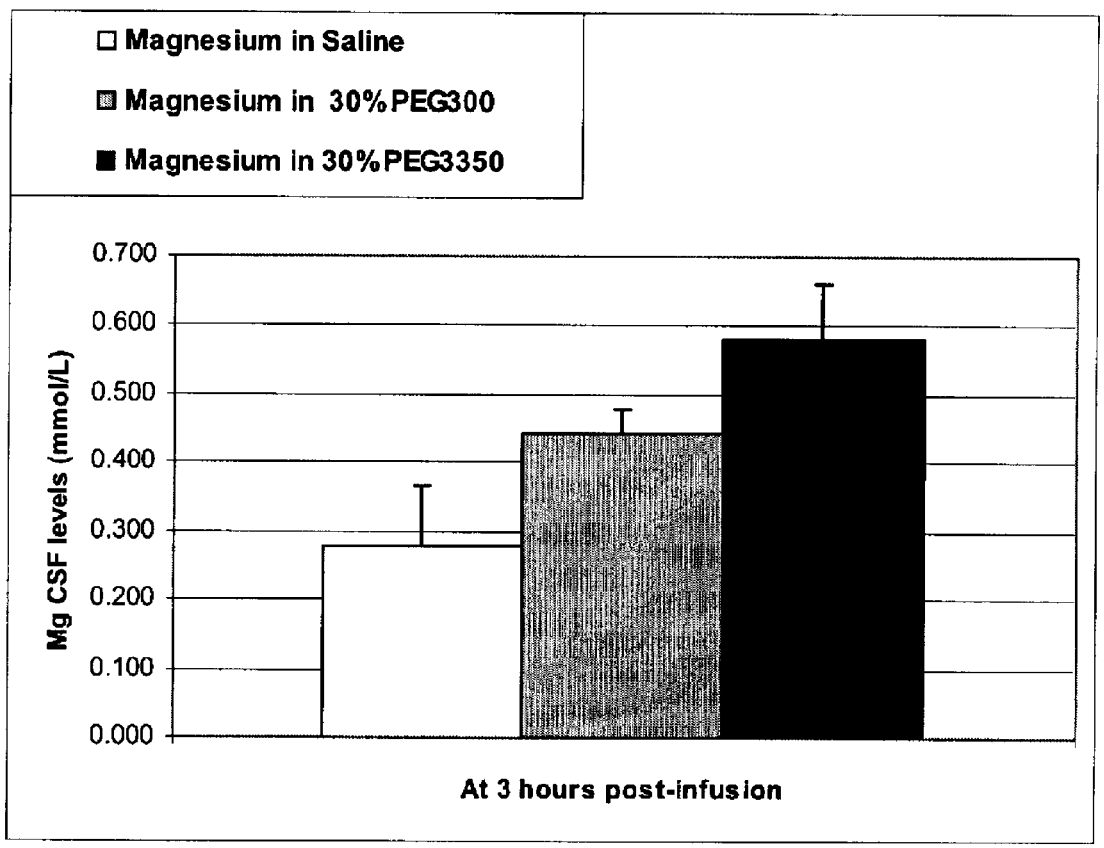
FIG. 4 presents a graph comparing CSF level of magnesium following parenteral administration of magnesium in formulations containing PEGs of various molecular weights.
Figure 5:
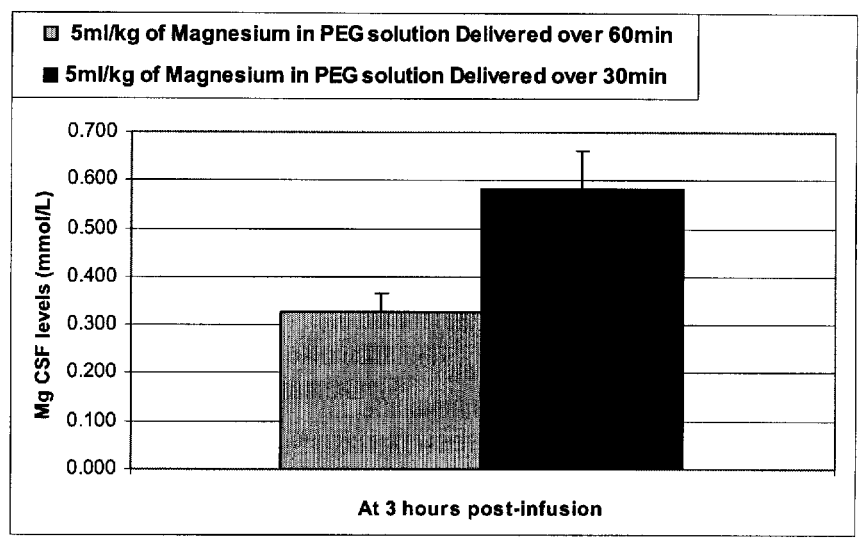
FIG. 5 presents a graph comparing CSF level of magnesium following parenteral administration of a magnesium in PEG solution delivered at various speeds.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION OF THE INVENTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent.

One aspect of the invention provides compositions for preferential distribution of active agents to an injury site. The term "injury site," as used herein, refers to an organ affected by a biological condition known to cause vessels supplying the organ to leak. Leaky blood vessels allow for abnormal entrance into or escape from the vessels of fluid substances, such as blood and protein rich exudates. Biological conditions known to cause leaks in the vessels include, but are not limited, to conditions that cause swelling such as acute inflammation that can be observed from a few hours to a few weeks after acute tissue or bone injuries or chronic inflammation that can evolve over years when associated with degenerative disease such as age-related macular degeneration and diabetic retinopathy or conditions that cause angiogenesis, such as cancer.

The instant compositions comprise a delivery ligand and at least one active agent where the interaction between the delivery ligand and the at least one active agent is mainly of an ionic nature. These interactions could be defined as a "chelation" like effect. Cations of the active agent may form electrostatic attraction to certain heteroatoms of the delivery ligand, for example, N, O, and S atoms, of the delivery ligand. Such binding sites are referred herein as chelation sites. For example, although the hydrophilic polymer PEG as a whole is non-ionic, the lone pairs of the electrons on the ether oxygens on the PEG chains imparts an anionic character to the polymer and can bind to a metal ion such as magnesium chloride through cations like $Mg^{2+}$ or $MgCl^+$. In one embodiment, the delivery ligand and the active agent are specifically selected so the interactions between them are mainly of an ionic nature so that the binding of the active agent of the delivery ligand and release of the active agent into the target site are not dependent on enzymatic activity.

Delivery ligands for the instant compositions may meet the following criteria: 1) they are water soluble; 2) they are rapidly cleared from the intact blood vessels and excreted; 3) they accumulate preferentially where the blood vessels leak; 4) they possess hydrophilic properties; and 5) they possess chelation sites suitable for ionic binding with cations.

As noted above, the delivery ligands may be rapidly excreted from the body when the blood vessels are intact. Accordingly, delivery ligands can have a half-life less than 3 hours, less than 2 hours or less than 1 hour. The rate of systemic clearance or half-life and excretion of a delivery ligand is related to the molecular weight of the ligand, with higher molecular weight ligands having longer half-lives. Furthermore, for the same molecular weight, hydrophilic ligands have shorter half-lives than more hydrophobic ligands. Hydrophilic ligands that can be excreted mostly unchanged through urine have shorter half-life than ligands that requires some transformation before excretion. For example, since 24,000 Da is the cut-off for glomerular filtration, any ligand heavier than 24,000 DA needs to be degraded to some extent before it can be excreted, which adds to its half-life. Accordingly, delivery ligands may be preferably selected from polymers with hydrophilic properties having a molecular weight of less than about 24,000 DA.

The delivery ligand may be selected from a hydrophilic or an amphipathic polymer. The term "hydrophilic polymer," as used herein, means any macromolecule (molecular weights of 200 daltons and greater) which exhibits an affinity for or attraction to water molecules and which comprises multiple instances of an identical subunit ("monomer") connected to each other in chained and/or branched structures. The hydrophilic polymer component may be a synthetic or naturally occurring hydrophilic polymer.

Naturally occurring hydrophilic compounds include, but are not limited to: proteins such as collagen and derivatives thereof, fibronectin, albumins, globulins, fibrinogen, and fibrin; carboxylated polysaccharides such as polymannuronic acid and polygalacturonic acid; aminated polysaccharides, particularly the glycosaminoglycans, e.g., hyaluronic acid, chitin, chondroitin sulfate A, B, or C, keratin sulfate, keratosulfate and heparin; methyl cellulose, sodium carboxylmethyl cellulose and activated polysaccharides such as dextran and starch derivatives.

Useful synthetic hydrophilic compounds include, but are not limited to: polyalkylene oxides, particularly polyethylene glycol and poly(ethylene oxide)-poly(propylene oxide) copolymers, including block and random copolymers; polyols such as glycerol, polyglycerol (particularly highly branched polyglycerol), poly(polyethylene glycol methacrylate), poly(glycerol methacrylate), poly(glycerol acrylatete), poly(polyethylene glycol acrylate), poly(alkyl oxazoline), phosphoryl choline polymers, sodium and potassium polymethacrylate, sodium and potassium polyacrylate, polymethacrylatic acid and polyacrylic acid, propylene glycol and trimethylene glycol substituted with one or more polyalkylene oxides, e.g., mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; acrylic acid polymers and analogs and copolymers thereof, such as polyacrylic acid per se, polymethacrylic acid, poly(hydroxyethylmethacrylate), poly(hydroxyethylacrylate), poly(methylalkylsulfoxide methacrylate), poly(methylalkylsulfoxide acrylate) and copolymers of any of the foregoing, and/or with additional acrylate species such as aminoethyl acrylate and mono-2-(acryloxy)-ethyl succinate; polymaleic acid; poly (acrylamides) such as polyacrylamide per se, poly(methacrylamide), poly(dimethylacrylamide), and poly(N-isopropylacrylamide); poly(olefinic alcohol)s such as poly(vinyl alcohol); poly(N-vinyl lactams) such as poly(vinyl pyrrolidone), poly(N-vinyl caprolactam), and copolymers thereof; polyoxazolines, including poly(methyloxazoline) and poly (ethyloxazoline); and polyvinylamines.

The term "amphipathic polymer," as used herein, refers to any macromolecule (molecular weights of 200 daltons and greater) which have localized quantum variations in charge giving rise to polar substructures and non-polar substructures. The polar substructures evidence an affinity for or attraction to other polar molecular structures such as water molecules (hydrophilic), while the nonpolar substructures exhibit an affinity or attraction for nonpolar molecules such as lipids, oils, greases, fats, etc. (lipophilic). Suitable amphipathic polymers include, but are not limited to, poloxamer P-188, polyetherester copolymers such as polyethylene glycol and polylbutylene terephthalate copolymers, polyethylene glycol and polypropylencoxide copolymers, polyethylene glycol and polypropylene glycol block copolymers.

Amphipathic polymers also include a family of polyetheramines known as Jeffamine®. These polyetheramines contain primary amino groups attached to the end of a polyesther backbone, which is typically based on propylene oxide (PO), ethylene oxide (EO), or a mixture thereof. The Jeffamine® family includes monamines, diamines, triamines and secondary amines. Jeffamine® may be procured from Huntsman Corporation, headquartered in The Woodlands, Tex.

In general, the concentration of the delivery ligand in the instant compositions range between about 10 and 60% weight per volume, i.e., 10 and 60 gm of ligand to 100 ml solution, between about 20 and about 40% weight per volume, or between about 30% and about 40% weight per volume. The concentration of the delivery ligand in the instant compositions depends on the number of chelation sites in the delivery ligand. The delivery ligands are composed of repeating subunits of one or more types, at least some of which include chelation sites. Delivery ligands with higher molecular weight are composed of a higher number of sub-units, and thus they are more likely to have a higher number of chelation sites than delivery ligands with lower molecular weight. Accordingly, as a general rule, the concentration of the delivery ligand with higher molecular weight in the composition may be lower than the concentration of the delivery ligand comprising the same sub-units and having a lower molecular weight. For example, when utilizing a delivery ligand with a molecular of 3350 DA, the composition preferably comprises at least 20% weight to volume of the delivery ligand. In another example, when utilizing a delivery ligand with a molecular of 300 DA, the composition preferably comprises at least 30% weight to volume of the delivery ligand.

In various embodiments, the delivery ligand may comprise polyethylene glycol (PEG). PEGs of molecular weights between about 100 and 20,000 DA, more preferably between about 300 to 9000 DA are suitable, and most preferably between about 2,000 DA and about 4,000 DA for use as delivery ligands in instant compositions. PEGs of different molecular weights may be obtained from, for example, Sigma-Aldrich, St. Louis, Mo., USA.

The term "active agent," as used herein, refers to a chemical element or compound that alleviates signs or symptoms of the biological condition affecting the targeted organ and causing vessels to leak. In some embodiments, the chemical structure of the delivery ligand and the active agent are selected so they can form a complex mainly based on interactions of ionic nature. The concentration of the active agent in the instant compositions may range between about 0.1% to about 20% weight per volume. In some embodiments, the concentration of the active agent in the instant compositions may range between 0.8 and 20% weight per volume.

In some embodiments, the active agent may be selected from metal ions, including, but not limited to, monodentate metal ions, such as potassium and lithium; bidentate metal ions, such as magnesium and calcium; transition metals, such as iron, zinc, and copper; more complex metal ions, such as aluminum; and compounds comprising such metal ions. Such metal ions form complexes with delivery ligands by forming ionic bonds through electrostatic attraction to certain heteroatoms of the delivery ligand, such as Nitrogen, Oxygen or Sulfur atoms. The type of ionic bond can vary including electron sharing between one or more metal ions and one or more subunits of the delivery ligand. The metal counterion may also participate in the formation of the complex with the delivery ligand.

In some embodiments, the instant compositions may also include hydrophilic disease-modifying agents, neurotransmitter, neuropeptides and neuronal receptor modulators, anti-inflammatory and immunomodulator agents, antioxidants, anti-apoptotic agents; nootropic and growth agents, modulators of lipid formation and transport, modulators of blood flow and vessel formation, analgesics, steroidal anti-inflammatory drugs such as corticosteroids, non-steroidal anti-inflammatory drugs such as salicylates, COX-2 inhibitors, TNF$\alpha$ inhibitors, opiates and morphinomimetics, among others.

In one embodiment, the bioactive agent comprises a magnesium compound. The concentration of magnesium in the instant compositions may range between about 0.1% to about 20% weight per volume, more preferably between about 0.1% to about 10% weight per volume. Most preferably the concentration of magnesium in the instant compositions is between about 0.4 and about 4% weight per volume and higher than the concentration of magnesium found in serum, buffer or electrolyte solutions which normally vary between 0-10 mM. Various magnesium salts may provide a source for the magnesium compounds. Suitable magnesium salts include, but are not limited to, magnesium sulfate, magnesium carbonate, magnesium chloride, magnesium oxide, magnesium hydroxide or any combination thereof. These compounds are readily available commercially from, for example, Sigma Aldrich, St. Louis, Mo., USA.

In addition to the delivery ligand and the active agents, the instant compositions may include one or more pharmaceutically acceptable carriers. The instant compositions may include excipients such as solvents, binders, fillers, disintegrants, lubricants, suspending agents, surfactants, viscosity increasing agents, buffering agents, antimicrobial agents, among others. Many different pharmaceutically acceptable carriers and excipients are known and disclosed, for example, in Remington's Pharmaceutical Sciences, Lippincott Williams & Wilkins; 21 edition (May 1, 2005).

By way of non-limiting examples, compositions disclosed in U.S. patent application Ser. Nos. 11/418,153 and 11/418, 152, incorporated herein by reference in their entireties, may be employed.

In some embodiments, the instant compositions are prepared for parenteral administration. Parenteral administration is generally characterized by a subcutaneous, intramuscular, or intravenous injection. Instant compositions for parenteral administration may be prepared as liquid solutions or suspensions, solid forms suitable for solution in liquid prior to injection.

Another aspect of the invention is directed to methods for preferential distribution of active agents to an injury site. Such methods comprise identifying a patient having an organ affected by a biological condition known to cause vessels supplying the organ to leak and administering to a patient a therapeutically effective amount of instant composition.

Yet another aspect of the invention is directed to methods of treating organs affected by one or more biological conditions known to cause vessels supplying the organ to leak by preferentially distributing one or more active agent(s) known to treat the one or more biological conditions. Such method comprises identifying a patient whose having such an affected organ and administering to the patient a therapeutically effective amount of instant composition.

The term "treating" or "treatment" refers to executing a protocol, which may include administering one or more drugs to a patient (human or otherwise), in an effort to alleviate signs or symptoms of the disease. Alleviation can occur prior to signs or symptoms of disease appearing, as well as after their appearance. Thus, "treating" or "treatment" includes "preventing" or "prevention" of the disease. In addition, "treating" or "treatment" does not require complete alleviation of signs or symptoms, does not require a cure, and specifically includes protocols which have only a marginal effect on the patient.

The term "therapeutically effective amount" means a quantity of the active agent which, when administered to a patient, is sufficient to result in an improvement in patient's condition. The improvement does not mean a cure and may include only a marginal change in patient's condition. It also includes an amount of the active agent that prevents the condition or stops or delays its progression. Generally, a therapeutically effective amount of the instant composition may be estimated based on patient's weight. In certain embodiments, patient preferably receives a dose of at least about 0.5 to about 20 ml of composition per kg of patient's weight, more preferably between about 0.5 and 10 ml and most preferably between about 1 and 8 ml of composition per kg of patient's weight. In one embodiment, the patient needs to a receive a dose of about 0.1 to about 3 g of delivery ligand and about 4 to about 80 mg of the active agent per kg of patient's weight, and most preferably between about 0.3 to about 2.5 g of the delivery ligand and about 8 to about 65 mg of the active agent per kg of patient's weight. Repeated doses may be administered if necessary. In some specific non-limiting embodiments, the composition administered to a patient may comprise PEG 3350 and magnesium chloride hexahydrate in the above listed amounts.

Any diagnosing method known and used in the art may be utilized to identify an organ affected by a biological condition known to cause vessels supplying the organ to leak. Suitable diagnosing methods include, but are not limited to, blood tests, urine tests, tissue swelling, pain, functional or neurological evaluations or medical imaging tests, such as X-ray, ultrasound, CAT scans or MRI.

As noted above, preferred delivery ligands are rapidly cleared from the intact blood vessels and excreted from the patient's body unless they accumulate at the site of leaky vessels. Because such ligands are likely to have a short half life in the body, they need to be administered to a patient rapidly. More specifically, it is desirable to administer a dose of the instant composition to the patient within two half-lives, and more preferably within one half-life, of the delivery compound. For example, in some PEGs having a molecular weight between 1000 and 6000 DA may be utilized. The half-lives of such PEGs in humans is between about 30 and about 90 minutes, and thus it is desirable to administer a dose of the instant composition comprising such PEGs within 180 minutes to take in account for individual variations and most preferably within 90 minutes. In another example, PEG of MW 3350 has a half-life of 29-42 minutes in rats and better preferential distribution is observed when the magnesium in the PEG 3350 solution is administered within a period less than 60 minutes.

Having now generally described the invention, the same may be more readily understood through the following reference to the following example, which is provided by way of illustration and is not intended to limit the present invention unless specified.

EXAMPLE

Methods and Tests Pertaining to Data in FIGS. 1-7:

Female Sprague-Dawley rats (Harlan Sprague-Dawley, Indianapolis, Ind.), weighing 250-300 grams each were given free access to food and water before the experiment. The animals were anesthetized with ketamine (80 mg/kg) and xylazine (10 mg/kg). Brain temperatures were monitored using a rectal thermometer. The animals' body temperature was maintained at 37° C. by using a water-jacketed heating pad. Brain temperature was monitored for 1 hour prior to injury to 6 hours following injury and was recorded at 30-minute intervals.

The spinal cord injury model utilized in the studies is described in detail (Rabchevsky et al, 2002). Young adult female Sprague-Dawley rats received a spinal cord contusion using the Precision Systems and Instrumentation, LLC (Fairfax Station, Va.) pneumatic impactor. Prior to surgery, rats were assigned to different treatment groups based on a randomized block design so that on any given surgery day all treatment groups were included. The rats were anesthetized with ketamine (80 mg/.kg) and xylazine (10 mg/kg) before laminectomy was performed at the $10^{th}$ thoracic vertebra ($T_{10}$). The vertebral column was stabilized with angled clamps on the upper thoracic (T8) and lumber (T11) levels and the impactor with a tip diameter of 2 mm was delivered at approximately 150 kdynes onto the exposed, intact dura overlying the dorsal spinal cord. The impactor was immediately removed, the wound irrigated with saline and the muscle and skin openings sutured together.

Two hours following injury, saline, 0.8% magnesium in saline or 0.8% magnesium in a 20 or 30% PEG 300 Da or 3350 Da formulations were administered by intravenous infusion of 5 mL/kg over a 10 to 60 minute period. The right jugular vein was cannulated with PE 50 tubing for iv administration. The cannula was secured through the back of the neck and capped between infusion periods. Animals were re-anesthetized for re-administration of compounds. The contents of the infusion vials were blinded to the investigators performing both the infusions and the analyses.

Methods and Tests Pertaining to Data in FIG. 8:

Systemic exposure and half-life of the PEG component was evaluated following daily intravenous administration of 10-20 ml/kg of 0.8% magnesium in 30% PEG3350 formulation delivered over 30 minutes in rats.

Methods and Tests Pertaining to Data in FIGS. 1-8:

At various time points after infusion, cerebrospinal fluid and/or blood samples and/or spinal cord tissue with and without the injury site were collected. The blood samples were processed to serum for the magnesium assay or to plasma for the PEG assay.

Serum and CSF samples were analyzed for magnesium concentrations by the Clinical Pathology Department at WIL Research Laboratories, LLC, 1407 George Road, Ashland, Ohio 44805. Serum and CSF samples were reacted with xylidyl blue in an alkaline solution containing ethyleneglycol-bis(2-aminoehtylether)-N,N,N',N'-tetraacetic acid (EGTA) to form a purple chromophore. The formation of the chromophore (and consequently a reduction of the xylidyl blue) is proportional to the concentration of $Mg^{2+}$, measured by the instrument as a decrease in the xylidyl blue absorbance (600 nm). A Hitachi 912 clinical chemistry analyzer assay was used for the determination of magnesium in serum and CSF.

Tissue and plasma concentrations of PEG-3350 in rat plasma were measured using a validated high performance liquid chromatograpy tandem mass spectrometry (HPLC/MS/MS) method in positive electrospray ionization mode. The method for the determination of PEG-3350 used acetonitrile to de-proteinize 200 μL of plasma. Following centrifugation of the plasma or tissue homogenate, the supernatant fraction from each sample was concentrated by evaporation and reconstituted with mobile phase A prior to analysis. The samples were analyzed with an HPLC/MS/MS assay using a Thermo Hypersil ODS column. The peak areas of PEG-3350 and the theoretical concentrations of calibration standards were fit to the ln-quadratic function, excluding the origin.

Results:

(1) PEG accumulates preferentially at the site of injury following parenteral administration.

Quantitative evaluation of PEG spinal tissue levels using HPLC/MS/MS assay also indicated that PEG accumulates preferentially at the site of injury with PEG tissue levels of 3198 ug/ml found at the site of injury 30 min post-infusion relative to 1238 ug/ml at a non-injured site. The PEG spine tissue levels rapidly decreased over time such as the 3 hours post-infusion 1431 ug/ml was found at the site of injury and 519 ug/ml at a non-injured site. These results are presented in FIG. 1. However, a certain amount of PEG must have remained at the site of injury because the PEG levels increased with the number of infusions. At 3 hours post-infusions, PEG tissue levels at the site of injury were 1431 ug/ml and 3891 ug/ml after one infusion and five infusions, respectively.

(2) PEG increases magnesium accumulation in the CNS compartment in SCI rats.

Magnesium levels in the cerebrospinal fluid (CSF) of SCI rats following intravenous administration of a magnesium in saline solution or magnesium in PEG solution were evaluated using a colorimetric assay. As presented in FIG. 2, thirty minutes after infusion, magnesium CSF levels were similar for both formulations and ranged from 0.29-0.34 mmol/L. However, three hours post-infusion, magnesium CSF levels were increased by two folds in the magnesium in PEG group (0.58 mmol/L) relative to no changes in the magnesium in saline group (0.28 mmol/L). Similarly to the PEG spinal tissue levels, the magnesium CSF levels increased with the number of magnesium in PEG infusions. At 3 hours post-infusions, magnesium CSF levels of 0.58 mmol/L after and 0.97 mmol/L were recorded after one and five infusions, respectively. As presented in FIGS. 3-5, the concentration and MW of the PEG component as well as the rate of delivery can influence the magnesium CSF levels achieved following intravenous administration of magnesium in PEG formulations.

(3) The PEG formulation does not affect the magnesium systemic clearance

Figure 6:
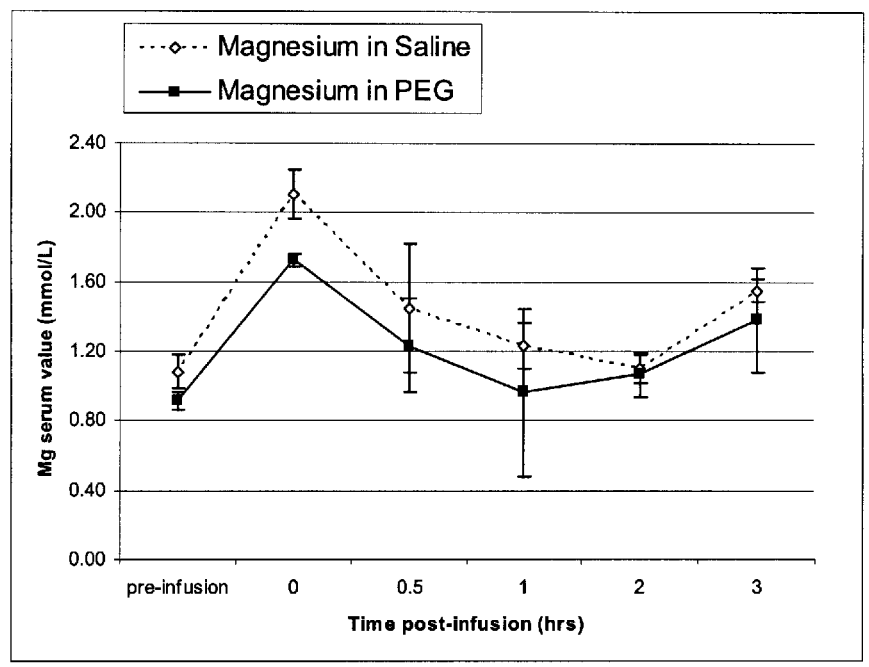
FIG. 6 presents a graph showing serum levels of magnesium following parenteral administration of magnesium in a saline or a PEG formulation initiated a few hours after injury.

Referring to FIG. 6, the formulation of magnesium in a PEG solution did not alter the systemic distribution of magnesium relative to magnesium in saline solution. Cmax levels were observed at the end of the infusion (t=0) and reached about 2.00 mmol/L following administration of magnesium in saline or magnesium in PEG solutions. Magnesium serum levels decreased rapidly over time and were back to baseline levels at around 1-2 hours post-infusion.

(4) PEG is rapidly cleared from the systemic circulation

Figure 7:
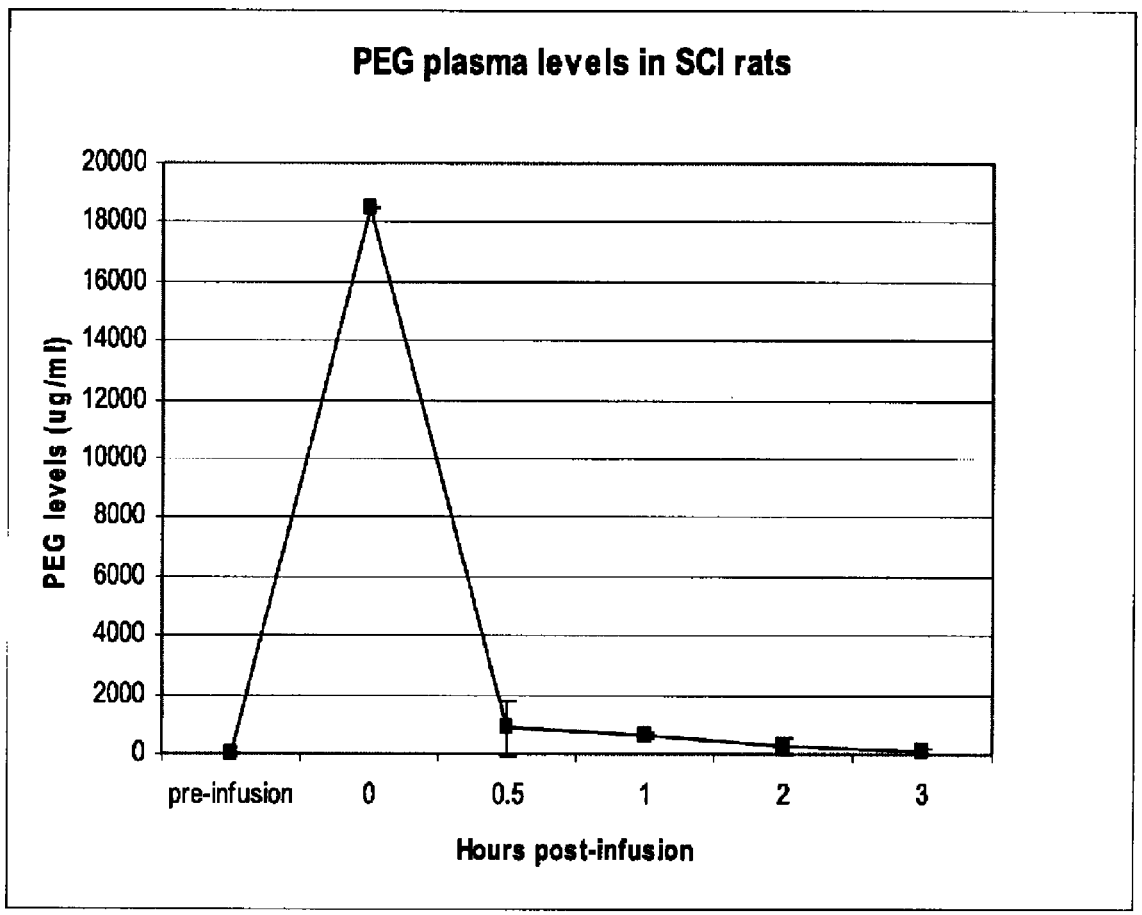
FIG. 7 presents a graph showing PEG plasma levels following administration of a magnesium in PEG formulation initiated a few hours after injury.

Referring to FIG. 7, in injured animals, the Cmax value for the PEG plasma level was observed at the end of the infusion and levels decreased rapidly to baseline level at 30 minutes post-infusion. Similarly in non-injured rats (FIG. 8), the Cmax value for the PEG plasma level was observed at the end of the infusion, levels decreased rapidly leading to half-lives that varied between 0.49-0.69 hours in female and male rats. Daily repeated infusions over 7 days did not affect the PEG systemic exposure and clearance profiles.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention which is defined by the following claims.

What is claimed is:

1. A method of increasing magnesium at a site of a spinal cord injury in a patient, the method comprising administering to the patient a composition comprising a delivery ligand comprising polyethylene glycol (PEG) having a molecular weight of between about 100 DA and about 20,000 DA and the polyethylene glycol comprises at least 30% weight per volume of the composition and the composition comprises about 0.4% to about 4% weight per volume of magnesium, and at least one dose of the composition is administered within one half-life of the delivery ligand wherein the half-life of the ligand is between about 30 and about 90 minutes.

2. The method of claim 1, wherein the composition comprises about 0.1 to about 3 g of ligand per kg of patient's body weight.

3. The method of claim 1, wherein the interaction between the delivery ligand and the magnesium is an ionic interaction.

4. The method of claim 1, wherein the site of the spinal cord injury comprises a leaky blood vessel.

5. The method of claim 1, wherein the polyethylene glycol comprises a molecular weight of between about 300 DA and about 9000 DA.

6. The method of claim 1, wherein the composition comprises about 8 to about 65 mg of the magnesium per kg of patient's body weight.

7. The method of claim 1, wherein the magnesium comprises magnesium sulfate, magnesium carbonate, magnesium chloride, magnesium hydroxide, magnesium oxide or a combination thereof.

8. A method of treating a spinal cord injury by increasing magnesium to the spinal cord injury, the method comprising administering a composition comprising a delivery ligand comprising polyethylene glycol (PEG) having a molecular weight of between about 100 DA and about 20,000 DA and the polyethylene glycol comprises between about 30% to about 60% weight per volume of the composition and the composition comprises about 0.4% to about 4% weight per volume of magnesium, and at least one dose of the composition is administered within two half-lives of the delivery ligand wherein the half-life of the ligand is between about 30 and about 90 minutes.

9. The method of claim 8, wherein the composition comprises about 0.1 to about 3 g of ligand per kg of patient's body weight.

10. The method of claim 8, wherein the interaction between the delivery ligand and the magnesium comprises an ionic interaction.

11. The method of claim 8, wherein the polyethylene glycol has a molecular weight of between about 300 DA and about 9000 DA.

12. The method of claim 8, wherein the composition comprises about 8 to about 65 mg of the magnesium per kg of patient's body weight.

13. The method of claim 8, wherein the magnesium comprises magnesium sulfate, magnesium carbonate, magnesium chloride, magnesium hydroxide, magnesium oxide or a combination thereof.

14. The method of claim 8, wherein the composition comprises about 30% of the delivery ligand.

15. The method of claim 1, wherein the composition is administered intravenously at a dose of about 0.5 ml to about 10 ml of the composition per kg of patient body weight.

16. The method of claim 1, wherein the polyethylene glycol comprises about 30% weight per volume of the delivery ligand.

17. The method of claim 1, wherein the polyethylene glycol comprises about 40% weight per volume of the delivery ligand.

18. The method of claim 1, wherein the composition is administered by subcutaneous, intramuscular, or intravenous injection.

19. The method of claim 1, wherein the composition is administered by intravenous injection.

20. The method of claim 1, wherein the polyethylene glycol comprises about 30% to about 40% weight per volume of the composition and the polyethylene glycol comprises a molecular weight of between about 300 DA and about 9000 DA.

21. The method of claim 20, wherein the magnesium comprises magnesium chloride.

22. The method of claim 8, wherein the composition comprises a first composition comprising polyethylene glycol and a second composition comprising magnesium, the first and second compositions being administered separately.

23. The method of claim 8, wherein a single dose of the composition is administered within a period less than 60 minutes.

24. The method of claim 8, wherein the PEG comprises PEG 3350, which comprises 30% of the composition.

25. The method of claim 8, wherein the PEG comprises PEG 3350, which comprises 30% of the composition and the composition comprises an antioxidant.

26. The method of claim 8, wherein the composition comprises an antioxidant.

* * * * *